United States Patent
Aleksandrova et al.

(10) Patent No.: US 8,999,710 B2
(45) Date of Patent: Apr. 7, 2015

(54) PROCESS FOR THE PREPARATION OF DISINFECTED HUMAN CELL SUSPENSIONS

(75) Inventors: Krasimira Aleksandrova, Hannover (DE); Marc Barthold, Hannover (DE); Lubomir Arseniev, Hannover (DE); Carsten Griesel, Ladenburg (DE); Christoph Priesner, Hannover (DE)

(73) Assignee: Cytonet GmbH & Co. KG, Weinheim (DE)

( * ) Notice: Subject to any disclaimer, the term of this patent is extended or adjusted under 35 U.S.C. 154(b) by 0 days.

(21) Appl. No.: 13/816,909

(22) PCT Filed: Jul. 30, 2011

(86) PCT No.: PCT/EP2011/003838
§ 371 (c)(1),
(2), (4) Date: Feb. 13, 2013

(87) PCT Pub. No.: WO2012/022429
PCT Pub. Date: Feb. 23, 2012

(65) Prior Publication Data
US 2013/0143324 A1 Jun. 6, 2013

(30) Foreign Application Priority Data
Aug. 14, 2010 (DE) .......... 10 2010 034 330

(51) Int. Cl.
*C12N 5/071* (2010.01)
*A01N 1/02* (2006.01)

(52) U.S. Cl.
CPC .............. *C12N 5/067* (2013.01); *A01N 1/0215* (2013.01); *C12N 2501/70* (2013.01); *C12N 2509/00* (2013.01)

(58) Field of Classification Search
USPC .................................................. 435/381, 41
See application file for complete search history.

(56) References Cited

U.S. PATENT DOCUMENTS

| 4,695,536 | A | 9/1987 | Lindstrom et al. |
| 5,741,782 | A | 4/1998 | Brockbank et al. |
| 2003/0021775 | A1 | 1/2003 | Freeman |
| 2004/0110289 | A1 | 6/2004 | Ludlow et al. |
| 2010/0047213 | A1 | 2/2010 | Zeitlin et al. |

FOREIGN PATENT DOCUMENTS

| EP | 0 889 690 | 1/1999 |
| WO | WO-92/12632 | 8/1992 |

OTHER PUBLICATIONS

Advanced BioMatrix. Collagenase, 50 mg from *Clostridium histolyticum* Catalog No. 5030. pp. 1-2. Downloaded from the world wide web on Apr. 5, 2013: <http://www.advancedbiomatrix.com/wp-content/uploads/2012/03/DFU_Collagenase_5030.pdf>.*
Pichard, Lydiane. Human Hepatocyte Culture. Methods in Molecular Biology. 2006. vol. 320. pp. 283-293.*
Worthington. Biochemical Corporation. Collagenase Product Information Catalog. Downloaded from the Worthington website on Sep. 27, 2013: <http://www.worthington-biochem.com/cls/cat.html>.*
ChemBlink. Collagenase: Product Catalog. Retreived from the ChemBlink website on Jul. 22, 2014: <http://www.chemblink.com/products/9001-12-1.htm>.*
Leeming, J.P. et al. Residual antibiotics in allograft heart valve tissue samples following antibiotic disinfection. Journal of Hospital Infection (60). 2005. pp. 231-234.*
Joerg C. Gerlach et al.; "Comparison of four methods for mass hepatocyte isolation from pig and human livers", Transplantation, Williams and Wilkins, Baltimore, US, vol. 57, No. 9, Jan. 1, 1994, pp. 1318-1322, XP009154462.
Krassimira Alexandrova, et al.; "Large-Scale Isolation of Human Hepatocytes for Therapeutic Application", Cell Transplantation, US, vol. 14, No. 10, Jan. 1, 2005, pp. 845-853, XP009154317.
Ragai R. Mitry et al.; "Human Hepatocyte Isolation and Relationship of Cell Viability to Early Graft Function", Cell Transplantation, US, vol. 12, No. 1, Jan. 1, 2003, pp. 69-74, XP009154318.
E. Fitzpatrick, et al.; "Human hepatocyte transplantation: state of the art", Journal of Internal Medicine, vol. 266, No. 4, Oct. 1, 2009, pp. 339-357, XP55012817.
Umberto Baccarani, et al.; "Isolation of Human Hepatocytes from Livers Rejected for Liver Transplantation on a National Basis: Results of a 2-year Experience", Liver Transplantation, Saunders, Philadelphia, PA, US, vol. 9, No. 5, May 1, 2003, pp. 506-512, XP008093068.
M. N. Berry, et al.; "High-Yield Preparation of Isolated Rat Liver Parenchymal Cells: A Biochemical and Fine Structural Study", The Journal of Cell Biology, vol. 43, No. 3, Dec. 1, 1969, pp. 506-520, XP55013428.
Thomas D. Lindquist, et al.; "Stability and Activity Vancomycin in Corneal Storage Media", 1993 Raven Press, Ltd., New York, Cornea, vol. 12, No. 3, pp. 222-227, 1993.

* cited by examiner

*Primary Examiner* — Susan Hanley
*Assistant Examiner* — Nghi Nguyen
(74) *Attorney, Agent, or Firm* — Jordan and Hamburg LLP

(57) ABSTRACT

In a process for preparing disinfected preparations from mammalian tissues, mammalian tissue is perfused at one step with an enzyme-free liquid antibiotic composition that includes at least one antibiotic and is contained in at least one perfusion buffer. In a step occurring after such one step, enzymatic antibiotic-free treatment of the tissue is carried out to obtain a single-cell suspension. In another step disinfected preparations are obtained.

4 Claims, No Drawings

PROCESS FOR THE PREPARATION OF DISINFECTED HUMAN CELL SUSPENSIONS

BACKGROUND OF THE INVENTION

The present invention relates to processes for the preparation of disinfected single-cell preparations and to the preparations thus prepared.

Liver transplants are the most important life-saving measure in the event of acute or chronic liver failure. In order to meet the need for transplant material, which cannot be covered by donor organs alone, methods other than complete organ transplantation have been developed in recent years, for example partial liver transplantation or the transplantation of liver cell preparations.

Single-cell preparations are of particular interest because they can be obtained from donor organs that are unsuitable for organ transplantation. In order to obtain hepatocytes from liver tissue, a two-step perfusion method is known which uses one collagenase-containing buffer and one EDTA-containing buffer (Berry and Friend, 1969, The Journal of Cell Biology, Vol. 43, pages 506-520). In said method, individual cells are enzymatically released from the tissue complex by perfusing the liver tissue with the collagenase-containing buffer.

Since the single-cell preparations obtained are medicaments, the microbial sterility must be ensured in each case. However, in approximately 70 to 80% of preparations, this is not the case since contamination usually already exists in the organ transport medium, which generally stems from the organ material or tissue material of the donor. However, with a product as valuable as human donor organs, it is desirable to obtain a large yield of transplantable tissue or cell preparations that are not microbially contaminated. Conventional decontamination processes such as heating, autoclaving, or irradiation make it impossible to maintain the viability of the cells, and, therefore, cannot be used to disinfect the tissue.

Processes for decontaminating tissue using antibiotics are likewise already known. These have been developed, for example, for storing corneal transplants (U.S. Pat. No. 4,695,536), or for decontaminating heart valve transplants (WO 92/12632 and EP 0 889 690). The exposure times to the antibiotic compositions used in said processes range from 24 hours to storage for several weeks. However, even an exposure time of 24 hours is unsuitable for highly sensitive tissue such as liver.

Furthermore, in said processes, only the surface is decontaminated. Another requirement placed on antibiotic-based decontamination processes for tissue and cells is that the process and the agents used therein should have no negative influence either on the obtaining of the liver cells or on the cell quality and viability thereof, and must be compatible with the sterility verification system used for quality control.

SUMMARY OF THE INVENTION

Therefore, the technical problem addressed by the present invention is that of providing processes for the gentle and effective decontamination, that is to say, disinfection, of tissues that overcome the disadvantages mentioned above, and particularly, processes that ensure a more effective and more rapid disinfection of the tissue under particularly gentle conditions, in particular, while at the same time maintaining the viability of the tissue or cells, even when said tissue or cells contained therein are highly sensitive, that is to say, originate from the liver, for example.

The technical problem addressed by the present invention is solved as follows. Namely, in one particularly preferred embodiment, the present invention accordingly relates to a process for the preparation of disinfected preparations, in particular single-cell preparations, from mammalian tissues, in particular human tissues, comprising the following process steps: a) perfusing mammalian tissue with a liquid antibiotic composition, b) carrying out an enzymatic treatment of the tissue, in particular to obtain a single-cell suspension, and c) obtaining disinfected preparations, in particular single-cell preparations, that is to say preparations in which the cells no longer exist in a tissue complex but rather are isolated from one another as individual cells or optionally as cell clusters or smaller cell aggregates. The invention therefore advantageously provides a process in which disinfected preparations, in particular single-cell preparations, preferably single-cell suspensions, can be prepared from tissues, that is, for example cell complexes or organs, of mammals, particularly humans, in an in vitro process. According to the invention, it is advantageously possible to obtain a cell preparation that is particularly suitable for accurate sterility testing. The procedure according to the invention therefore allows sterility testing that provides a high degree of accuracy regarding the sterility of the preparations obtained.

The invention proceeds from provided mammalian tissues that may originate for example from living or dead mammals, particularly mammals that have just recently died. In one particularly preferred embodiment, mammals are understood to mean humans or animals, for example livestock or laboratory animals, in particular pigs, cows, horses, dogs, cats, sheep, goats, monkeys, primates, birds, or rodents.

The tissue, in particular cell complexes or organs, taken from the donor mammals and provided in this way for the present invention, is used as a starting material in the present invention. The invention provides that tissue thus provided is brought into contact with an antibiotic composition and perfused, preferably using the vascular system intrinsic to the tissue, in particular intrinsic to the organ. The invention further provides that, either during or subsequent to the perfusion of the tissue with the antibiotic composition, the tissue is subjected to an enzymatic treatment, in the course of which the tissue complex is disbanded and a single-cell suspension is obtained. In this way, the antibiotic composition contains single cells that can accordingly be antibiotically treated in a particularly effective manner and thus disinfected.

In connection with the present invention, a single-cell preparation or a single-cell suspension is to be understood to mean, in particular, a preparation or suspension in which the cells exist individually and have no permanent physical contact with one another. In a further embodiment, a single-cell preparation or a single-cell suspension is also understood to mean that most of the cells that are present, in particular more than 50%, more than 60%, more than 70%, more than 80%, more than 90%, or more than 95% of the cells, are detached from one another and have no permanent physical contact with one another, and the remainder of the cells adding up to 100% exist in the form of cell clusters, smaller or larger cell aggregates, and residues of the tissue complex that have not fully been disbanded.

In connection with the present invention, a perfusion is to be understood to mean, in particular, a tissue perfusion, that is to say the flowing of a liquid, that is to say the present antibiotic composition, through a hollow organ or the vessels, in particular blood vessels, contained in the tissue. In connection with the present invention, a perfusion is a particularly preferred type of incubation.

In connection with the present invention, tissue is to be understood to mean a cohesive complex of cells, in particular having the same function and/or morphology, in particular also an organ, for example a liver, an organ part, a tissue complex, or section material, in particular from the liver, in particular liver section material. According to the invention, the tissue used is liver tissue, for example, a full liver or a part thereof, for example, liver section material. The single-cell suspensions prepared according to the invention are preferably liver cell suspensions.

In one particularly preferred embodiment, it is provided to carry out process step a) jointly, that is to say simultaneously or in a temporally overlapping manner, with process step b), that is the perfusion is carried out using an antibiotic composition that is preferably contained in at least one perfusion buffer, wherein at the same time at least one perfusion buffer contains at least one enzyme for the enzymatic treatment of the tissue to obtain a single-cell suspension. However, it is also preferred to carry out the perfusion first using an enzyme-free, antibiotic composition that is preferably contained in at least one perfusion buffer and then to carry out an enzymatic, antibiotic-free treatment according to step b), during which the tissue complex is disbanded and single cells of the tissue used in step a) are obtained, so that fully disinfected single cells are obtained in process step c).

According to the invention, it may also be provided in an optional process step to rinse the surface of the tissue used, prior to the perfusion according to the invention, with an antibiotic composition, preferably the antibiotic composition used according to the invention, in particular without perfusing said tissue, that is to say to carry out a primary decontamination of the surface. The incubation time for this is preferably only 5 to 60 minutes, preferably 5 to 45 minutes, and particularly preferably 5 to 30 minutes. With such a short incubation time, an antibiotic concentration that is higher than during the perfusion may optionally also be used. In one embodiment of the present invention, the rinsing of the surface may also be carried out during process steps a) and/or b).

The enzymatic treatment of the tissue to obtain a single-cell suspension, which is provided according to the invention, preferably uses at least one or preferably at least two enzymes that are in a preferably aqueous solution, in particular a buffered solution, in particular in a preferred embodiment, in the liquid antibiotic composition. The enzymes used for the enzymatic treatment are able to disband the tissue complex, in particular to dissolve cell/cell contacts and cell/extracellular matrix contacts, and to prepare therefrom a single-cell suspension without damaging or destroying the cells. In a preferred embodiment according to the invention, particularly suitable enzymes are collagenases, proteinases, and mixtures thereof. In connection with the present invention, a proteinase is also understood to mean a protease.

Preference is given to mixtures of collagenase and protease, in particular neutral proteases, in a ratio of enzymatic activities of 1 unit of collagenase to 40 to 60, preferably 50, units of protease.

Therefore, for each perfusion, use is preferably made of approximately 2000 to 4000 Wünsch units of collagenase in combination with 100,000 casein units or with 400 to 2500 clostridiopeptidase I units.

In one particularly preferred embodiment of the process according to the invention, the tissue is therefore perfused in vitro with the antibiotic composition that is preferably contained in at least one perfusion buffer and that contains at least one enzyme for disbanding the tissue into single cells, in particular contains a) at least one collagenase, or b) at least one collagenase and at least one proteinase, in particular a neutral proteinase. This leads to the disinfection and detachment of individual cells from the tissue complex and thus to obtaining disinfected single-cell preparations. Alternatively, in another preferred embodiment, the collagenase or the collagenase and proteinase may be contained separately from the at least one antibiotic active agent, preferably the antibiotic active agents, in the at least one perfusion buffer, preferably a phosphate/HEPES buffer, in a separate solvent, for example a buffer, and may be used separately from the antibiotic perfusion step, that is to say subsequently.

According to the invention, the antibiotic composition used according to the invention exists in liquid form, for example as a solution or suspension, preferably as an aqueous solution or suspension, particularly preferably in at least one perfusion buffer.

In one particularly preferred embodiment, the liquid antibiotic composition comprises at least one, preferably at least two, in particular at least three, preferably at least four or even more different antibiotics. These may be selected from the group consisting of the non-penicillins of the β-lactam antibiotics, aminoglycosides, glycopeptide antibiotics, and polypeptide antibiotics.

In one preferred embodiment, the antibiotic composition used according to the invention has no negative or inhibitory effect on the enzymatic treatment used, in particular the collagenase or proteinase treatment.

In one preferred embodiment of the present invention, it may be provided that the antibiotic composition is free of collagenases and proteinases.

The antibiotic composition, in particular an antibiotic combination that is preferably used according to the invention, is advantageously characterized in that this has no negative effect on the vitality and morphology of the isolated cells.

The at least one antibiotic, in particular the antibiotics, are contained in the composition according to the invention in quantities at which the growth, the multiplication, and/or the viability of microorganisms such as bacteria, preferably those that occur in donor organ transport media, is substantially reduced or inhibited, while the viability of the tissue or cells is substantially maintained.

In connection with the present invention, an antibiotic composition is to be understood to mean a substance composition that has antibiotic efficacy. In connection with the present invention, an antibiotic efficacy is to be understood to mean a harmful effect, in particular an antimicrobial harmful effect, such as killing, inhibiting reproduction, reducing reproduction, inhibiting growth, or reducing growth, in particular a killing effect on microorganisms, in particular bacteria, and specifically both gram-positive and gram-negative aerobic and anaerobic bacteria, fungi, protozoa, or reproduction products thereof, such as spores or germs. With particular preference, the antibiotic composition is particularly effective against microorganisms that occur in or on mammalian donor tissue or organs or in the transport media thereof.

In connection with the present invention, an antibiotic efficacy is therefore preferably to be understood to mean that microorganisms are killed, that is to say the antibiotic composition has a microbicidal, preferably bactericidal, effect. According to the invention, in one embodiment of the invention, the antibiotic efficacy need not necessarily be associated with a microbicidal effect, but rather can also mean that the microorganisms are merely limited in terms of their vital functions, for example growth, metabolism, or reproduction, that is to say a microbiostatic, in particular, a bacteriostatic, effect occurs.

In connection with the present invention, the term antibiotic efficacy is also preferably understood to mean a disinfecting effect, that is to say the antibiotic composition particularly preferably has a disinfecting effect, that is to say makes the materials used, for example tissue and/or cells, free of living microorganisms, preferably entirely or almost entirely, or kills said microorganisms. The disinfection encompasses not only the removal or killing of germs, that is to say early developmental stages of a microorganism, but also of all other developmental stages of microorganisms including the permanent forms thereof or infectious parts of the microorganisms. A disinfection is also to be understood to mean a significant reduction in the number of reproductive microorganisms, in particular such that the residual content of reproductive microorganisms in one unit of the disinfected product is at most $10^{-6}$ colony-forming units. In connection with the present invention, a disinfection is also to be understood to mean a decontamination.

In one particularly preferred embodiment, the liquid antibiotic composition is contained in at least one perfusion buffer.

Therefore, the present invention relates to a process in which use is made of an antibiotic composition comprising, preferably consisting of, non-penicillins of the β-lactam antibiotics, aminoglycosides, glycopeptide antibiotics, and/or polypeptide antibiotics in preferably at least one perfusion buffer. The antibiotic composition used according to the invention is suitable, in particular suitable and intended, for the in vitro disinfection of mammalian tissue and mammalian cells, preferably human tissue, organs, or organ parts, and human cells, in particular liver tissue and liver cells. The disinfection of the isolated tissue is achieved by perfusion with the antibiotic composition used according to the invention, use being made of the natural vascular system. As a result, a microbial disinfection of the entire tissue, including inner tissue and tissue that is difficult to access, and not only of the surface thereof, is achieved. This is particularly important especially in the case of the liver since in dying patients bacteria pass through the intestinal walls to varying degrees and thus are possibly washed by perfusion via the portal system of the organ to be removed. Retrograde contamination may also occur via the biliary system, which is physiologically in open contact with the intestinal flora. Despite optimal working techniques, such contamination will therefore never be fully prevented and makes gentle and effective decontamination with the antibiotic composition used according to the invention particularly necessary. In addition, such "internal" contamination may in some circumstances lead to the situation whereby the pathogens in the transport medium are at first unable to be detected but rather are released only in the course of the enzymatic dissociation of the tissue material. A disinfection of the isolated tissue by perfusion with the antibiotic composition according to the invention therefore advantageously leads to an early elimination of such "internal" contaminations. Thus, without adding antibiotics, almost 100% of the liver cell preparations, prepared from liver organs using contaminated transport medium, are likewise contaminated. However, by virtue of the decontamination according to the invention, liver cell preparations that are more than 65% disinfected were able to be prepared.

Preferably, the tissue is perfused in at least one perfusion step, preferably two, three, four, or more perfusion steps, for example three steps. In one preferred embodiment, in each case 3 to 5 liters of antibiotic-containing and/or collagenase/proteinase-containing perfusion buffer, preferably a phosphate/HEPES buffer, are used for each perfusion step. With particular preference, in the case of three perfusion steps, all three perfusion buffers, preferably first an EGTA- or EDTA-containing phosphate/HEPES buffer and then twice a phosphate/HEPES buffer, contain antibiotics, the collagenase/proteinase preferably being used only in the last perfusion step. It is also particularly preferred, in the case of three perfusion steps, that only the first two perfusion buffers contain antibiotics and that the collagenase/proteinase is used in the last perfusion step in an antibiotic-free perfusion buffer.

In one particularly preferred embodiment, the antibiotic composition is contained in at least two perfusion buffers, in particular two perfusion buffers, in particular or namely at least one EGTA- or EDTA-containing phosphate/HEPES buffer and at least one phosphate/HEPES buffer or other suitable buffer solutions.

The perfusion buffers used for the perfusion, that is to say for flowing through the tissue material, are preferably phosphate/HEPES (2-(4-(2-hydroxyethyl)-1-piperazinyl)-ethanesulfonic acid) buffers, but also EGTA (ethylene glycol-bis-(aminoethylether)-N,N'-tetraacetic acid)- or EDTA (ethylenediaminetetraacetic acid)-containing phosphate/HEPES buffers. The perfusion buffers used preferably have a physiological pH value of 7 to 8, particularly preferably 7.3 to 7.8, in particular 7.5.

In one particularly preferred embodiment, both the perfusion time and the enzymatic treatment time are each 10 to 360 minutes, preferably 20 to 240 minutes, in particular 30 to 120 minutes. In one particularly preferred embodiment, the perfusion and the enzymatic treatment of the tissue preferably take place jointly, in particular for a duration of 10 to 360 minutes, preferably 20 to 240 minutes, in particular 30 to 120 minutes.

In a further particularly preferred embodiment, the temperature both for the perfusion and for the enzymatic treatment is 9 to 39° C., preferably 10 to 37° C., in particular 25 to 37° C. In one preferred embodiment, during the perfusion and possibly the enzymatic treatment, the temperature of the antibiotic perfusion composition and of the perfused organ is increased, particularly preferably from a starting temperature in the region of less than 10° C., for example 4° C. to 10° C., to a final temperature in the range from 30° C. to 39° C., for example 37° C.

In one particularly preferred embodiment of the present invention, the antibiotic composition used contains a) at least one collagenase or b) at least one collagenase and at least one proteinase, in particular a neutral proteinase. Due to the presence of collagenase or collagenase and proteinase, a dissociation of the tissue material is achieved during the incubation, in particular perfusion, and thus single-cell suspensions can be obtained.

In one preferred embodiment, the present invention also provides a process for disinfecting a tissue or for preparing a disinfected mammalian cell preparation in vitro, wherein: a) the mammalian tissue is perfused with the antibiotic composition according to the present invention under suitable conditions, in particular for a suitable duration at a suitable temperature: b) an enzymatic treatment to prepare a single-cell suspension from the tissue is carried out in a temporally overlapping manner, that is to say at least for a given duration simultaneously, or subsequently; and c) a disinfected cell preparation is obtained.

In one particularly preferred embodiment of the present invention, it is provided to subsequently subject the disinfected cell preparations obtained by way of the process according to the invention to at least one, for example one, two, three, or more, washing step(s), isolating step(s), or both, which reduces the concentration of the antibiotics, enzymes, or both that are used, or which completely or almost completely removes these from the preparations obtained. With particular preference, after process step b), for example before or after process step c), one or more washing step(s) are carried out, preferably using an antibiotic-free washing buffer. This advantageously leads to the situation whereby the antibiotics and enzymes used in the process according to the invention are completely or almost completely removed, and the single-cell preparations obtained are suitable for subsequent sterility testing.

In one preferred embodiment, it may be provided that the disinfected cell preparations obtained are cryopreserved for storage purposes. To this end, the preparations are stored at a suitable low temperature in a medium suitable for cryopreservation.

Advantageously, it has been possible to show according to the invention that, by virtue of the process according to the invention, a higher cell yield (total number of cells obtained), a higher specific cell yield (number of cells per gram of liver tissue used), and a greater vitality of the isolated disinfected liver cells (proportion of living cells in suspension) could be achieved in a considerably faster time.

The use of the antibiotic composition employed according to the invention advantageously enables disinfected single-cell preparations, in particular preferably cell suspensions in, for example, culture media, which were not previously obtainable, in particular from liver cells, to be obtained in a particularly quick, gentle and effective manner from, for example, donor organs that are available for transplantation but are not suitable for this purpose.

The procedure according to the invention has the advantage that the antibiotic treatment that is carried out does not impair an enzymatic treatment, in particular a collagenase and/or proteinase treatment, that is carried out either simultaneously or subsequently, and moreover also does not have a negative effect on sterility checks that are subsequently carried out. In one particularly preferred embodiment, the antibiotic compositions used according to the invention are therefore suitable for the preparation of disinfected cell suspensions from tissues, that is to say not single cells in media that exist in the tissue or organ complex. For perfusing the isolated mammalian tissue or the isolated organ, the antibiotic composition that is used according to the invention and that is contained in at least one perfusion buffer is used in volumes that are preferably tailored to the size of the tissue or organ. These volumes can be determined empirically, as is known to the person skilled in the art.

The present invention also relates to disinfected cell preparations, that is to say cells, cell suspensions, or single-cell suspensions from mammals, that were prepared by one of the processes of the present invention.

The invention will be explained in more detail in the following examples. The examples are not to be understood as limiting, but rather the intention is for the advantages of the invention to be explained in more detail and to be illustrated on the basis of specific examples.

DETAILED DESCRIPTION OF THE INVENTION

Examples

Example 1

Preparation of Disinfected Liver Cell Suspensions with Simultaneous Antibiotic and Enzyme Treatment A. Execution To prepare disinfected liver cell suspensions from a liver, the following antibiotic composition was prepared:

The antibiotics were added in the following concentrations to all the perfusion buffers mentioned:

| ANTIBIOTIC | CONCENTRATION |
|---|---|
| MEROPENEM | 0.2 mg/ml |
| VANCOMYCIN | 0.05 mg/ml |

A multi-donor liver organ unsuitable for whole organ transplantation was first surface-rinsed for 30 min at room temperature using 5 L of antibiotic-containing phosphate/HEPES buffer and then was perfused in three steps with the following volumes of antibiotic-containing buffers, pH 7.25-7.45:

1. 5 L of EDTA-containing phosphate/HEPES buffer, perfusion 10 min, 20-40° C.;
2. 5 L of phosphate/HEPES buffer, perfusion 10 min, 25-40° C.;
3. 3 L of collagenase/protease-containing phosphate/HEPES buffer, perfusion 24 min, 25-40° C.

Collagenase/protease concentration: combination of 2000 Wünsch units of collagenase I and 400 to 2500 units of protease (clostridiopeptidase I).

The perfusion time with the enzyme- and antibiotic-containing buffers was 44 min in total. The natural blood vessel system of the liver used was used for the perfusion.

During the perfusion, the temperature of the perfused organ and of the surrounding environment was slowly increased from <10° C. to 37° C. (buffer temperature between room temperature and 40° C.).

After being isolated from the tissue, the cells were washed multiple times with antibiotic-free buffer until the antibiotic concentration was less than $\frac{1}{1000}$ of the antibiotic concentration used.

A sample for sterility checking was taken both from the transport medium in which the organ was delivered and from the disinfected cell suspension after cryopreservation.

B. Results

The following microorganisms were detected in the transport medium: Enterobacter cloacae, Acinetobacter baumannii, wherein the time taken during the automatic incubation until microbial growth was noted, the so-called "Time to positivity", was 1.67 h.

In the cell suspension disinfected according to the invention, no germs could be detected after cryopreservation, even after 14 days of incubation.

A sterility test can be carried out with the prepared cell suspensions after a sufficient number of washing steps using antibiotic-free buffer.

Example 2

Preparation of Disinfected Liver Cell Suspensions with Sequential Antibiotic and Enzyme Treatment A. Execution A multi-donor liver organ unsuitable for whole organ transplantation was first surface-rinsed for 8 min at room temperature using 5 L of phosphate/HEPES buffer having a double antibiotic concentration and then was perfused in two steps with antibiotic-containing buffers, and in a further step, with collagenase-containing and antibiotic-free buffer, in the following volumes, pH 7.25-7.45:

1. 5 L of EDTA-containing phosphate/HEPES buffer, perfusion 68 min, 20-40° C.;
2. 5 L of phosphate/HEPES buffer, perfusion 10 min, 25-40° C.;

3. 3 L of collagenase/protease-containing and antibiotic-free phosphate/HEPES buffer, perfusion 24 min, 25-40° C.

Collagenase/protease concentration: combination of 2000 Wünsch units of collagenase 1 and 400 to 2500 units of protease (ciostridiopeptidase I).

The perfusion time with the enzyme- and antibiotic-containing buffers was 102 min in total. The natural blood vessel system of the liver used was used for the perfusion.

During the perfusion, the temperature of the perfused organ and of the surrounding environment was slowly increased from <10° C. to 37° C. (buffer temperature between room temperature and 40° C.).

After being isolated from the tissue, the cells were washed multiple times with antibiotic-free buffer until the antibiotic concentration was less than $1/1000$ of the antibiotic concentration used.

A sample for sterility checking was taken both from the transport medium in which the organ was delivered and from the disinfected cell suspension after cryopreservation.

B. Results

Staphylococcus Aureus was able to be detected in the transport medium. The time taken during the automatic incubation until microbial growth was noted, the so-called "Time to positivity", was 3.85 h.

In the cell suspension disinfected according to the invention, no germs could be detected after cryopreservation, even after 14 days of incubation.

A sterility test can be carried out with the prepared cell suspensions after a sufficient number of washing steps using antibiotic-free buffer.

The invention claimed is:

1. A process for preparing disinfected, single-cell suspension preparations from mammalian tissue, comprising:
   prior to any enzymatic treatment of said mammalian tissue, performing a primary decontamination of a surface of the mammalian tissue comprising rinsing the mammalian tissue to obtain a rinsed mammalian tissue;
   after said primary decontamination, perfusing said rinsed mammalian tissue with an enzyme-free liquid antibiotic composition that comprises at least one antibiotic and is contained in at least one perfusion buffer, wherein the enzyme-free liquid antibiotic composition is perfused through vascular tissue inherent to the mammalian tissue to obtain an antibiotic-treated mammalian tissue;
   subsequent to all antibiotic perfusion, carrying out an enzymatic antibiotic-free treatment of the tissue to obtain the disinfected, single-cell suspension preparations comprising contacting said antibiotic-treated mammalian tissue with collagenase I and clostridiopeptidase I to obtain disinfected single-cell suspension preparations;
   washing the obtained disinfected single-cell suspension preparations with an antibiotic-free washing buffer to obtain a washed disinfected single-cell suspension preparation;
   subsequent to said washing step, and without an intervening antibiotic treatment, performing a microbiological sterility test of the washed disinfected single-cell suspension preparation; and
   wherein said washing is adapted to either one of reduce or eliminate said antibiotic from said disinfected single-cell suspension so as not to have a negative effect on said microbiological sterility test.

2. The process according to claim 1, wherein the tissue is liver tissue.

3. The process according to claim 1, wherein a time duration of said perfusing is 30 to 120 min and wherein temperature of the enzyme-free liquid antibiotic composition is increased during the perfusion.

4. The process according to claim 1, wherein the enzyme-free liquid antibiotic composition is contained in at least two perfusion buffers, at least one of the perfusion buffers being an EGTA- or EDTA-containing phosphate/HEPES buffer and at least one other of the buffers being a phosphate/HEPES buffer.

* * * * *